United States Patent
Bishop et al.

(10) Patent No.: US 9,352,863 B1
(45) Date of Patent: May 31, 2016

(54) SYSTEM AND METHOD FOR SHIPPING AN ITEM

(75) Inventors: Lynn Marie Bishop, Tusin, CA (US); Frank Zuniga, Lake Elsinore, CA (US); William Kenneth Robinson, Mira Loma, CA (US); Reginald Lawrence Vasseur, Jr., Valenica, CA (US); Jack Thompson, III, Fontana, CA (US)

(73) Assignee: LUCE COMMUNICATIONS LLC, Mira Loma, CA (US)

( * ) Notice: Subject to any disclaimer, the term of this patent is extended or adjusted under 35 U.S.C. 154(b) by 1192 days.

(21) Appl. No.: 12/233,508

(22) Filed: Sep. 18, 2008

Related U.S. Application Data (60) Provisional application No. 60/973,430, filed on Sep. 18, 2007.

(51) Int. Cl.
*B42D 15/00* (2006.01)
*B65D 79/00* (2006.01)
*B65B 27/06* (2006.01)
*A61B 10/00* (2006.01)

(52) U.S. Cl.
CPC ............ *B65B 27/06* (2013.01); *A61B 10/0096* (2013.01); *B42D 15/00* (2013.01); *B65D 79/00* (2013.01)

(58) Field of Classification Search
CPC .... A61B 10/0096; B65D 27/06; B65D 79/00; B42D 15/00
USPC ......... 206/223, 216, 569, 570, 204, 232, 456, 206/460; 229/68.1, 300–304, 92.8, 71, 72
See application file for complete search history.

(56) References Cited

U.S. PATENT DOCUMENTS

| | | | |
|---|---|---|---|
| 4,240,547 A | | 12/1980 | Taylor |
| 4,720,017 A | | 1/1988 | Pestes |
| 4,949,840 A | | 8/1990 | Brown |
| 5,150,971 A | | 9/1992 | Strong et al. |
| 5,607,101 A | * | 3/1997 | Saito ............... 229/72 |
| 5,611,433 A | | 3/1997 | Levy |
| 5,620,097 A | * | 4/1997 | Timmons et al. ........... 206/521 |
| 5,921,396 A | * | 7/1999 | Brown, Jr. ................. 206/223 |
| 5,996,799 A | | 12/1999 | Garreth et al. |
| 6,447,463 B1 | * | 9/2002 | Borkowski ............... 206/223 |
| 6,467,642 B2 | | 10/2002 | Mullens et al. |

(Continued)

FOREIGN PATENT DOCUMENTS

DE 19621785 A1 12/1996
JP 9292392 A 11/1997

(Continued)

OTHER PUBLICATIONS

English abstract of JP92-92392A published on Nov. 11, 1997 espacenet database, 2 pages.

(Continued)

*Primary Examiner* — Andrew Perreault
(74) *Attorney, Agent, or Firm* — Osha Liang LLP (57) ABSTRACT

A system including a substrate with an adhesive panel, a shipping item removably attached to the adhesive panel, and a package envelope including the shipping item removably attached to the adhesive panel, where a location of the adhesive panel within the package envelope renders the package envelope suitable for an automated handling process of a shipping authority.

12 Claims, 6 Drawing Sheets

(56) References Cited

U.S. PATENT DOCUMENTS

| | | | |
|---|---|---|---|
| 6,491,160 B2* | 12/2002 | Butler et al. | 206/232 |
| 6,569,676 B1 | 5/2003 | Tripp et al. | |
| 6,921,370 B2 | 7/2005 | Zhou et al. | |
| 6,928,793 B2* | 8/2005 | Rutledge | 53/449 |
| 6,953,207 B2* | 10/2005 | Raming | 206/232 |
| 6,978,891 B2 | 12/2005 | Rutledge | |
| 7,128,352 B1 | 10/2006 | Phippen | |
| 7,243,796 B2* | 7/2007 | Grablick | 206/460 |
| 7,264,776 B2 | 9/2007 | Guo et al. | |
| 2003/0008467 A1 | 1/2003 | Kai et al. | |

FOREIGN PATENT DOCUMENTS

| | | |
|---|---|---|
| JP | 2000241055 A | 9/2000 |
| JP | 2002215789 A | 8/2002 |
| JP | 2004125408 A | 4/2004 |
| WO | 9515493 A1 | 6/1995 |
| WO | 2007068277 A1 | 6/2007 |

OTHER PUBLICATIONS

English abstract of DE 000019621786 A1 published on May 12, 1996, espacenet database, 2 pages.

English abstract of JP 02-215789 published on Aug. 2, 2002, espacenet database, 2 pages.

English abstract of JP 00-241055 published on Sep. 8, 2000, espacenet database, 2 pages.

English abstract of JP 04-125408 published on Apr. 22, 2004, espacenet database, 2 pages.

"Hair Drug Test Kit Follicle", Medimpex United Inc., http://www.meditests.com/hairdrugtest.html, Sep. 11, 2007, 2 pages.

"Medaus Saliva Test Kits", Medaus Pharmacy, htttp://www.medaus.com/p/401.html, Sep. 11, 2007, 3 pages.

"Personal Saliva Hormone Profile Test Kits", Osteoporosis, Menopause, Hormone Health Products, http://www.osteoporosis-med.com/testkit.htm, Sep. 11, 2007, 3 pages.

Ochnio, JJ et al., Particpant-collected, Mail-delivered Oral Fluid Specimans can Replace Traditional Serosurveys: A Demonstration-of-feasibility Survey of Hepatitis A Virus-specific Antibodies in Adults., Canadian Journal of Public Health, http://www.ncbi.nlm.nih.gov/pubmed/17278676, Jan.-Feb. 2007, 1 page.

Winer, R., "Concordance of Self-Collected and Clinician-collected Swab Samples for Detecting Human Papillomavirus DNA in Women 18 to 32 years of age", Department of Epidemiology, University of Washington Seattle, Jun. 2007, 10 pages.

Levy, Sharon., A Review of Internet-Based Home Drug-Testing Products for Parents, American Academy of Pediatrics, Apr. 4, 2004, 9 pages.

"Home DNA Test Kits", http://www.homedna-test.com, DNA Testing Centre, Sep. 11, 2007, 5 pages.

* cited by examiner

SYSTEM AND METHOD FOR SHIPPING AN ITEM

CROSS-REFERENCE TO RELATED APPLICATIONS

This application claims priority under 35 U.S.C. §119(e) to U.S. Provisional Application Ser. No. 60/973,430, filed on Sep. 18, 2007, and is hereby incorporated in its entirety.

BACKGROUND OF INVENTION

The United States Postal Service (USPS) provides an effective way ship items between a source and a destination. The USPS classifies all types of mail and charges various postage rates accordingly. The classifications range from automated flat to priority mail and express post, with many classes in-between. Even within automated flat, many subclasses such as first class or standard mail exist. However, in contrast to other classes of mail, automated flat mail is handled by a machine at the mail distribution center. Accordingly, all shipping items destined for automated flat processing must meet certain requirements addressing size, weight, and/or flexibility. Further, items that are not flexible may need to be secured for shipping. These challenges make it difficult to ship items having even minimal thickness using automated flat mail.

SUMMARY OF INVENTION

In general, in one aspect, the invention relates to a system. The system comprises a substrate comprising an adhesive panel; a shipping item removably attached to the adhesive panel; and a package envelope comprising the shipping item removably attached to the adhesive panel, wherein a location of the adhesive panel within the package envelope renders the package envelope suitable for an automated handling process of a shipping authority.

In general, in one aspect, the invention relates to a method. The method comprises obtaining a shipping item; obtaining a substrate comprising an adhesive panel; obtaining a package envelope; attaching the shipping item to the adhesive panel; and inserting the substrate into the package envelope after attaching the shipping item, wherein a location of the adhesive panel within the package envelope renders the package envelope suitable for an automated handling process of a shipping authority.

In general, in one aspect, the invention relates to a method. The method comprises receiving a package envelope comprising a reply envelope and a shipping item removably attached to an adhesive window of a substrate, wherein a location of the adhesive panel within the package renders the package envelope suitable for an automated handling process of a shipping authority; and shipping the reply envelope.

Other aspects of the invention will be apparent from the following description and the appended claims.

DETAILED DESCRIPTION

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more through understanding of the invention. However, it will be apparent to one of ordinary skill in the art that the invention may be practiced without these specific details. In other instances, well-known features have not been described in detail to avoid unnecessarily complicating the description.

In general, embodiments of the invention provide a system and method for shipping an item in a package envelope using a substrate having an adhesive panel. A location of the adhesive panel within the package envelope renders the package envelope, including the item, suitable for automated flat shipping. In general, embodiments of the invention provide a system and method for shipping an item that is removably attached to the adhesive panel of a substrate. The adhesive panel is outside the handling zone of the shipping authority, rendering a package envelope, including the substrate and item, suitable for automated flat shipping.

Figure 1:
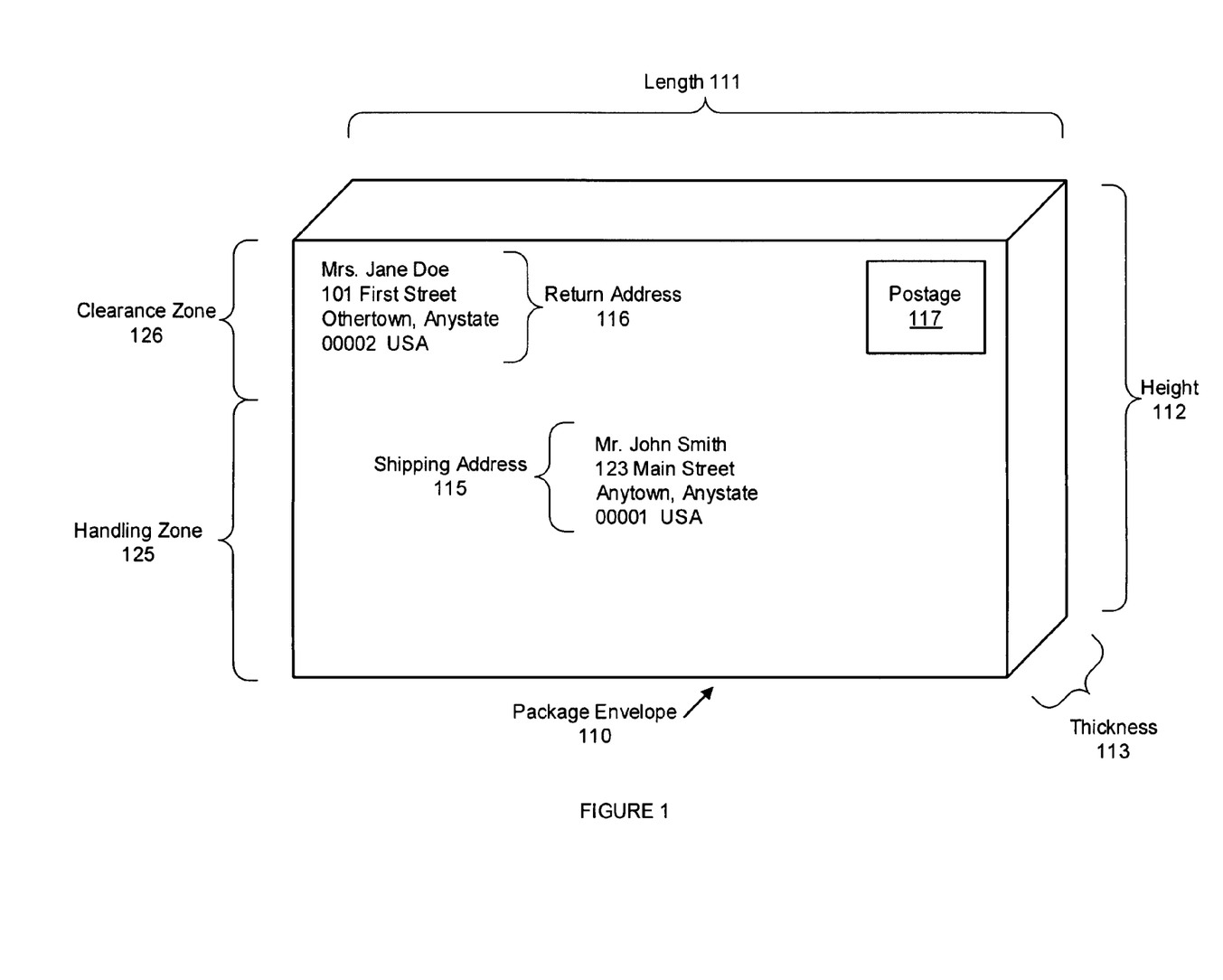
FIG. 1 shows a package envelope in accordance with one or more embodiments of the invention.

FIG. 1 shows a package envelope (110) in accordance with one or more embodiments of the system. The package envelope (110) is a container to ship one or more items (i.e., shipping items) from a source to a destination. As shown in FIG. 1, the volume of the package envelope (110) is described using three dimensions: a length (111), a height (112), and a thickness (113). Accordingly, it is these dimensions that define the size and shape of items that can be shipped using the package envelope (110).

Still referring to FIG. 1, the destination of the package envelope (110) is identified by a shipping address (115). The shipping address (115) may be printed directly on the package envelope (110), or may be placed inside the package envelope (110) and made viewable from the exterior of the package envelope (110) by replacing a portion of the package envelope (110) with a transparent material (e.g., plastic) (not shown). In contrast, the source or origin of the package envelope (110) is identified by a return address (116). Like the shipping address (115), the return address (116) may be printed directly on the package envelope (110).

In one or more embodiments of the invention, the package envelope (110) is shipped to its destination using a shipping authority. The shipping authority may be the Unites States Postal Service (USPS), or a private courier. The cost of shipping the package envelope (110) depends on many factors including, for example, the length (111), the height (112), and the thickness (113) of the package envelope (110); the mass of the package envelope (110) and its contents; and/or a distance between the source and the destination. In one or more embodiments of the invention, the cost of shipping the package envelope (110), reflected by the postage (117), is further dependent on whether the package envelope (110) qualifies for automated handling by the shipping authority, or whether the package envelope must be processed manually. Those skilled in the art, having the benefit of this detailed description, will appreciate that for a package envelope (110) of a given size and weight, it is cheaper to ship the package envelope (110) using an automated handling process of the shipping authority. In other words, manual processing is more expensive than automated processing.

Those skilled in the art, having the benefit of this detailed description, will appreciate that in an automated handling process, the shipping authority uses one or more machines to grip, move, and/or sort the package envelope (110). Specifically, the machines are in physical contact with one or more portions of the packaging envelope (110). In one or more embodiments of the invention, the machines are only in contact with portions of the packing envelope (110) inside the handling zone (125). All portions of the packing envelope (110) outside the handling zone (125) (i.e., the clearance zone (126)) will have less physical contact with the machine. Accordingly, in order to qualify for automated handling, the contents of the package envelope (110) overlapping the handling zone (125) must not interfere with the operation of the machines. Similarly, fragile content or portions of the content that are fragile, should be kept outside the handling zone (125).

In addition to handling zone (125) requirements, automated handling processes have additional requirements. For example, the dimensions (111, 112, 113) of the package envelope (110) must be neither too small nor too large to qualify for automated handling. Further, the mass of the package envelope (110) must be neither too light nor too heavy to quality for automated handling. Further still, the contents of the package envelope (110) must be secured in place to avoid excessive shifting during the automated handling process. Finally, the package envelope (110) must be neither too flexible nor too rigid to qualify for an automated handling process.

Automated flat processing is an automated handling process offered by the USPS. In one or more embodiments of the invention, in order to qualify for automated flat processing, the package envelope (110) must satisfy the requirements of at least one of two sorting machines: Automated Flat Sorting Machine (AFSM) 100 and/or Upgraded Flat Sorting Machine (UFSM) 1000.

In regard to the AFSM 100 requirements, the length (111) of the package envelope (110) must be no less than 6" and no more than 15". The height (112) of the package envelope must be no less than 5" and no more than 12". The thickness of the package envelope (110) must be no less than 0.009" and no more than 0.75". Further, the weight of the must be less than 13 ounces for first-class and less than 16 ounces for standard mail. Lastly, contents overlapping the handling zone (125) of the package envelope (110) must not disrupt the AFSM 100.

In regard to the UFSM 1000 requirements, the length (111) of the package envelope (110) must be no less than 4" and no more than 15.75". The height (112) of the package envelope (110) must be no less than 4" and no more than 12". If the package envelope (110) is less than 5" long, the thickness (113) of the package envelope (110) must be greater than 0.25". If the package envelope (110) is at least 5" long, the thickness (113) of the package envelope (110) must be at least 0.009". If the package envelope (110) is 13" long or less, the maximum thickness (113) of the package envelope (110) must be 1.25". If the package envelope (110) exceeds 13", the maximum thickness (113) of the package envelope (110) must be ⅞". Further, the weight of first class must not be more than 13 ounces, while the weight of standard mail must be less than 16 ounces. Lastly, contents overlapping the handling zone (125) of the package envelope (110) must not disrupt the UFSM 1000.

Figure 2:
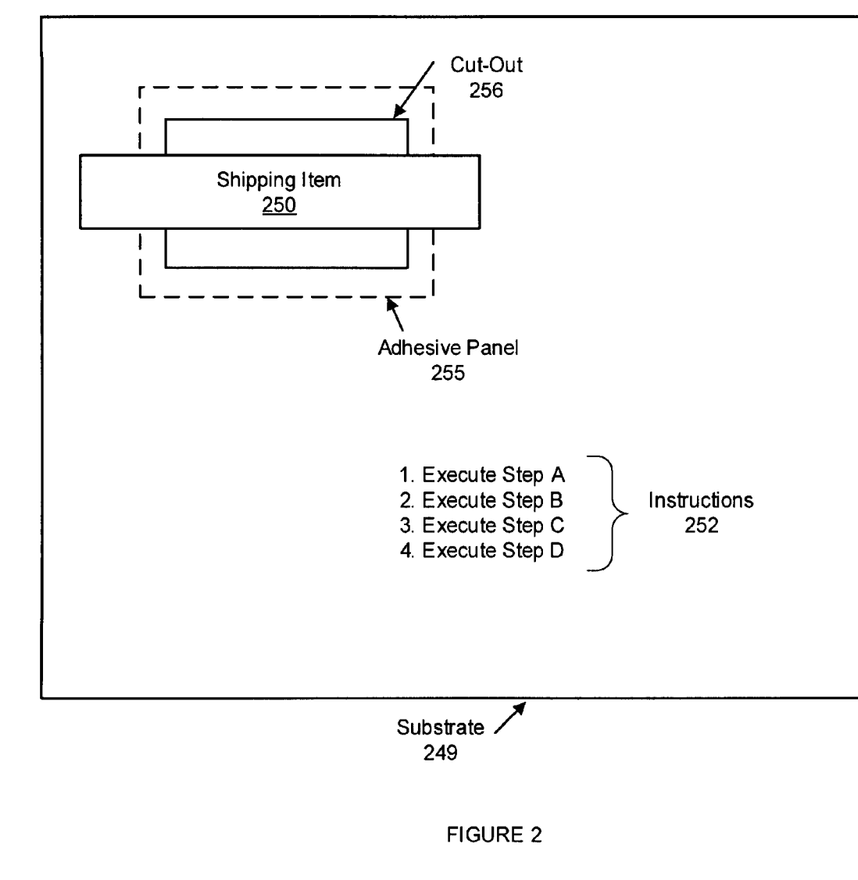
FIG. 2 shows a substrate in accordance with one or more embodiments of the invention.

FIG. 2 shows a substrate (249) in accordance with one or more embodiments of the invention. As shown in FIG. 2, the substrate (249) includes an adhesive panel (255) for attaching a shipping item (250) (i.e., an item to be shipped using the package envelope (110), discussed above in reference to FIG. 1). Although the adhesive panel (255) is shown as rectangular, those of ordinary skill in the art, having the benefit of this detailed description, will appreciate the adhesive panel (255) may be of any shape or size. In one or more embodiments of the invention, it is the texture, weight, and footprint of the shipping item (250) that dictate the material, shape, and size of the adhesive panel (255).

In one or more embodiments of the invention, the shipping item (250) is removably attachable to the adhesive panel (255). In other words, the material of the adhesive panel (255) must be such to allow the attachment and future removal of the shipping item (250) without damaging the shipping item (250) or damaging any label attached to the shipping item (not shown). Further, while the shipping item (250) is attached to the adhesive panel (255), the attachment must be of sufficient strength to secure the shipping item (250) in place regardless of the orientation of the substrate with respect to the ground.

In one or more embodiments of the invention, the adhesive panel (255) is deposited on the surface of the substrate (249). Alternatively, the adhesive panel (255) is placed on the back side of the substrate (249), and a cut-out (256) in the substrate exposes the adhesive panel (255).

In one or more embodiments of the invention, the shipping item (250) is a specimen-holding receptacle (SHR) for collecting and storing a specimen (e.g., a soil sample, a paint sample, a rock sample, a blood sample, a stool sample, etc.). Further, the substrate (249) is a sheet of paper including printed instructions (252) for using the shipping item (250) (i.e., for collecting the specimen). Those skilled in the art, having the benefit of this detailed description, will appreciate that the shipping item (250) may actually be any number of products, including a pen, a pencil, a coin, a piece of candy, a key, a credit card, etc.

Figure 3:
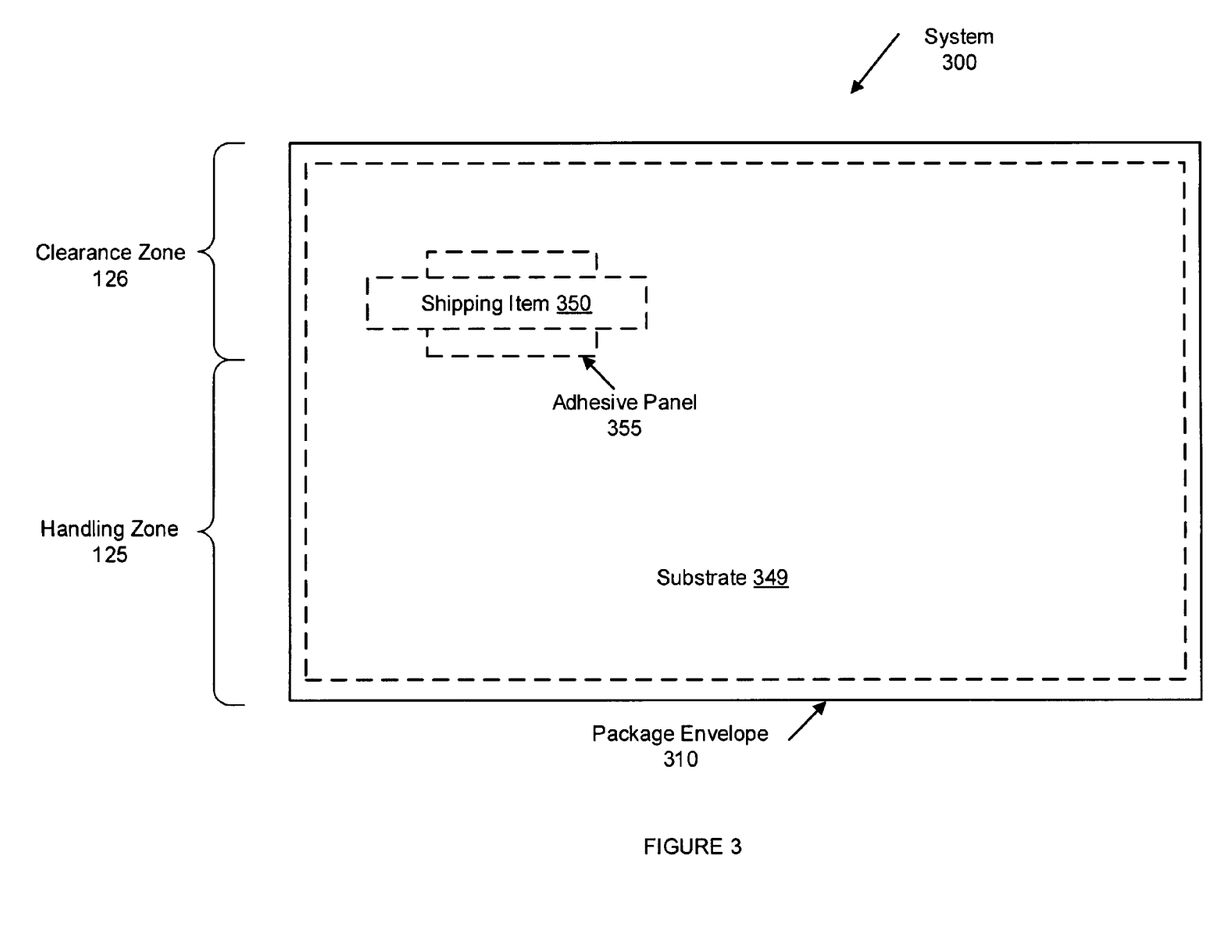
FIG. 3 shows a system in accordance with one or more embodiments of the invention.

FIG. 3 shows a system (300) in accordance with one or more embodiments of the invention. As shown in FIG. 3, the system includes a shipping item (350) removably attached to an adhesive panel (355) of a substrate (349). The shipping item (350), the adhesive panel (355), and the substrate (349) may be essentially the same as the shipping item (250), the adhesive panel (255), and the substrate (249) discussed above in reference to FIG. 2. The substrate (349), including the shipping item (350), is situated within a package envelope (310). The package envelope (310) may be essentially the same as the package envelope (110) discussed above in reference to FIG. 1.

Still referring to FIG. 3, the location of the adhesive panel (355) within the package envelope (310) keeps the shipping item (350) outside the handling zone (125) (discussed above in reference to FIG. 1). Accordingly, the shipping item (350) would not interfere with the machines used in an automated handling process and the package envelope (310) satisfies at least the handling zone requirements of the automated handling process. Thus, assuming the system (300) also satisfies the size, weight, and flexibility requirements of the automated handling process, the package envelope (310), including the shipping item (350), qualify for the automated handling process offered by a shipping authority.

Although one or more mentioned embodiments of the invention focus on a single item attached to a single adhesive panel, other embodiments of the invention may include substrates with any number of items attached to any number of adhesive panels. Further, although one or more mentioned embodiments of the invention focus on a package envelope having only a substrate with an attached item, other embodiments of the invention may include package envelopes having advertisements, instruction sheets, postage-paid reply envelopes, and/or biohazard bags (e.g., for storing/shipping a SHR after collecting a specimen) in addition to the substrate and the item.

Figure 4:
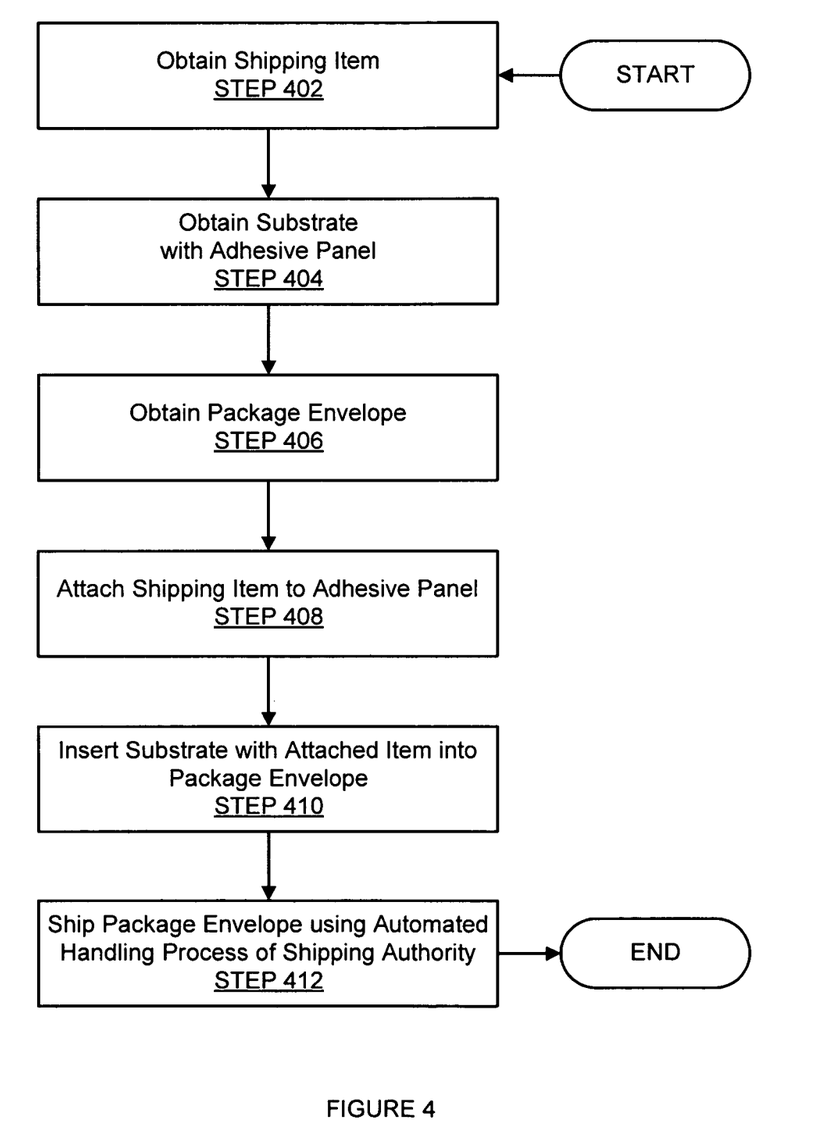
FIG. 4 shows a flowchart in accordance with one or more embodiments of the invention.

FIG. 4 shows a flowchart in accordance with one or more embodiments of the invention. The process shown in FIG. 4 may be used to ship an item using an automated handling process of a shipping authority. Those skilled in the art, having the benefit of this detailed description, will appreciate that the sequence of steps shown in FIG. 4 may differ among embodiments of the invention, and that one or more of the steps may repeated or skipped.

Initially, the item to be shipped (i.e., the shipping item) is obtained (STEP 402). As described above, this item may be a wide variety of products including, for example, a pen, a pencil, a coin, a piece of candy, a key, a credit card, a specimen-holding receptacle for collecting a specimen, etc. Further, the item must not violate the weight and/or size requirements associated with the automated handling processes of a shipping authority.

IN STEP 404, a substrate with an adhesive panel is obtained. The adhesive panel may be located on a surface of the substrate. Alternatively, the adhesive panel may be attached to the back side of the substrate. A cut-out within the substrate exposes the adhesive panel. The substrate may include printed instructions and/or advertisements.

In one or more embodiments of the invention, the adhesive panel must be positioned on the substrate such that the item, when attached to the adhesive panel, is kept external to the handling zone of the automated handling process. In other words, the item must be kept in the clearance zone of the automated handling process.

In STEP 406, a package envelope is obtained. The package envelope may be composed of any material, size, or shape, providing it does not violate the requirements associated with the automated handling process. Further, the package envelope may include both the shipping address and the return address to identify the source/origin and destination of the item to be shipped.

In STEP 408, the item is attached to the adhesive panel of the substrate. This step may be done manually or it may be automated. Regardless of whether STEP 408 is executed automatically or manually, the attachment must be of sufficient strength to secure the item during the movement, bumps and other things encountered during shipping. However, it must be possible to remove the item without damaging the item (i.e., the item must be removably attached to the adhesive panel).

In STEP 410, the substrate with the attached item is inserted into the package envelope. As discussed above, the location of the adhesive panel within the package envelope must keep the item outside the handling zone of the automated handling process.

In other or more embodiments of the invention, instruction sheets, advertisements, reply envelopes, and/or biohazard bags for storing/shipping a SHR are also inserted into the package envelope. However, the resulting weight and size of the packaging envelope must not violate the requirements of the automated handling process.

In STEP 412, the package envelope is shipped using an automated handling process of the shipping authority. For example, the package envelope may be shipped using automated flat processing offered by the USPS.

Although the process shown in FIG. 4 is heavily discussed from the sender's perspective, those skilled in the art, having the benefit of this detailed description, will appreciate that one or more steps described in FIG. 4 may be captured from the receiver's perspective.

Figure 5A:
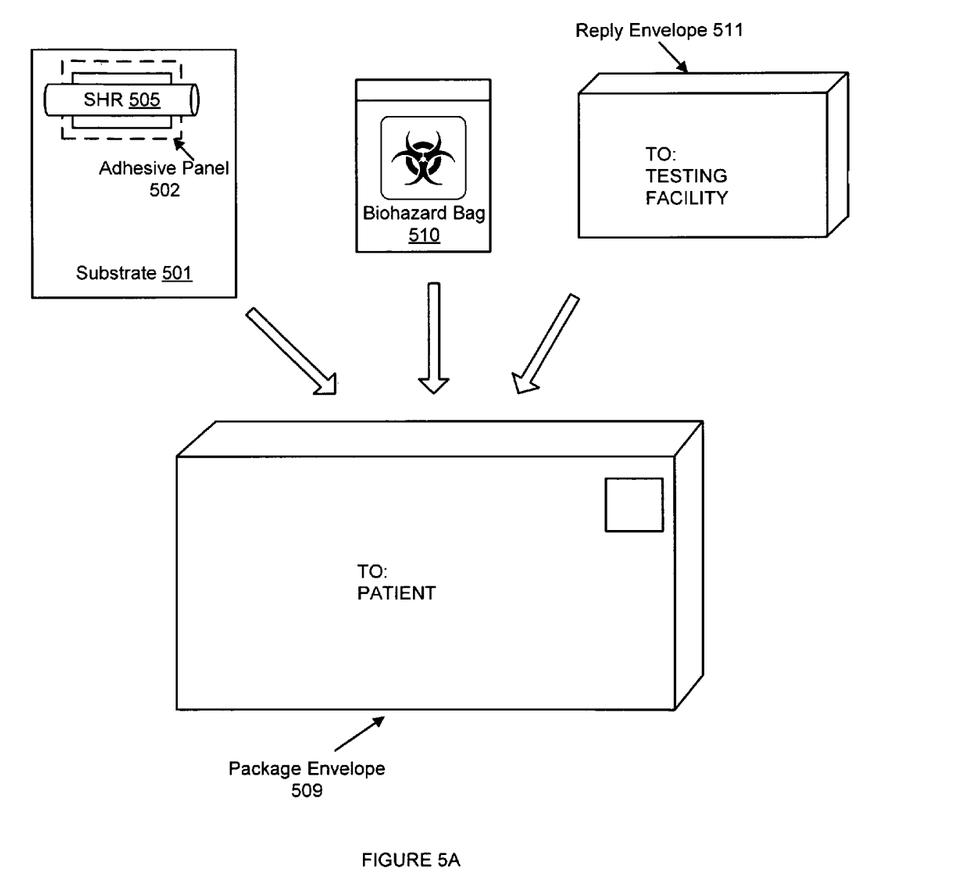
FIGS. 5A and 5B show an example in accordance with one or more embodiments of the invention.
Figure 5B:
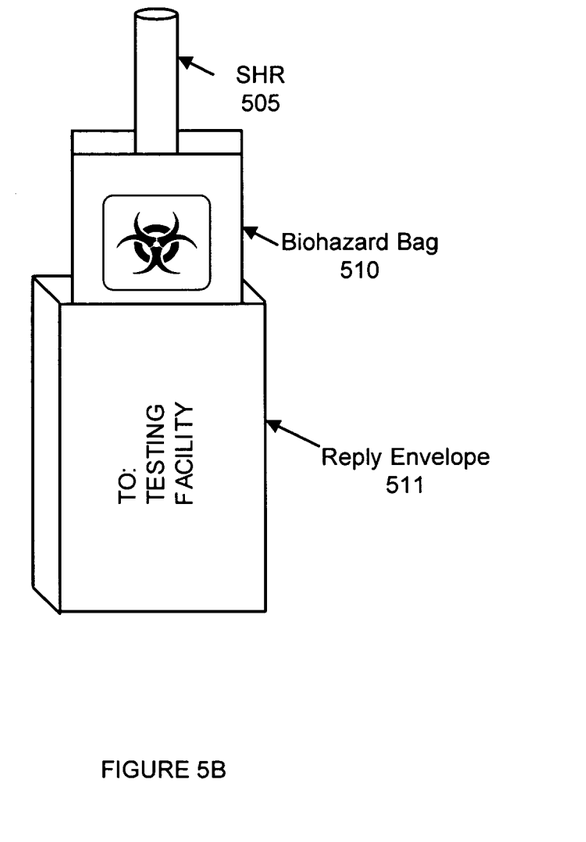

FIGS. 5A and 5B show an example in accordance with one or more embodiments of the invention. As shown in FIG. 5A, a substrate (501) includes an adhesive panel (502). Further, a SHR (505) is removably attached to the adhesive panel (502). The substrate (501), with the a removably attached SHR (505), a biohazard bag (510), and a reply envelope (511) are inserted into a package envelope (509). The location of the adhesive panel (502) within the package envelope (509) renders the package envelope (509) suitable for shipping using an automated flat processing service of the USPS. In other words, the location of the adhesive panel (502) within the package envelope (509) keeps the SHR (505) external to the handling zone of the package envelope (509). This reduces the cost of sending the package envelope (509).

Once the package envelope (509) is received by the patient, the SHR (505) is removed from the adhesive panel (502), and a stool sample is collected using the SHR (505). As shown in FIG. 5B, the SHR (505), including the stool sample, is first inserted into the biohazard bag (510) from the package envelope (509). Subsequently, the biohazard bag (510), now including the SHR (505), is inserted into the reply envelope (511) and shipped to the testing facility.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A system, comprising:
   a substrate comprising a cut-out;
   an adhesive panel positioned on a first side of the substrate and exposed on a second side of the substrate by the cut-out;
   a container configured to store a biological specimen, positioned on the second side of the substrate, and removably attached to the adhesive panel exposed by the cut-out; and
   a package envelope addressed to a patient and comprising:
      a handling zone for automated flat processing by a shipping authority,
      a clearance zone outside the handling zone, and
      a reply envelope addressed to a testing facility and configured to store the container after the biological specimen is placed into the container by the patient,
   wherein the container is empty and within the clearance zone after the substrate with the container removably attached to the adhesive panel is inserted into the package envelope.

2. The system of claim 1, wherein the shipping authority is the United States Postal Service.

3. The system of claim 1, wherein the adhesive panel comprises a triangle shape.

4. The system of claim 1, wherein the substrate comprises printed instructions for using the container.

5. The system of claim 1, wherein the package envelope further comprises a biohazard bag to hold the container within the reply envelope during shipping to the testing facility.

6. A method, comprising:
   obtaining a substrate comprising a cut-out and an adhesive panel positioned on a first side of the substrate and exposed on a second side of the substrate by the cut-out;

obtaining a container configured to store a biological specimen;

obtaining a package envelope addressed to a patient and comprising a handling zone for automated flat processing by a shipping authority and a clearance zone outside the handling zone;

obtaining a reply envelope addressed to a testing facility and configured to store the container after the biological specimen is placed into the container by the patient;

positioning the container on the second side of the substrate and removably attaching the container to the adhesive panel exposed by the cut-out; and inserting the reply envelope and the substrate with the container removably attached to the adhesive panel into the package envelope, wherein the container is empty and within the clearance zone after inserting the reply envelope and the substrate into the package envelope.

7. The method of claim 6, wherein the shipping authority is the United States Postal Service.

8. The method of claim 6, wherein the substrate comprises printed instructions for using the container.

9. The method of claim 6, further comprising inserting a biohazard bag into the package envelope to hold the container during shipping to the testing facility.

10. A method, comprising:

receiving a package envelope addressed to a patient and comprising a reply envelope addressed to a testing facility, a substrate having a cut-out, an adhesive panel positioned on a first side of the substrate and exposed on a second side of the substrate by the cut-out, and a container configured to store a biological specimen positioned on the second side of the substrate and removably attached to the adhesive panel, wherein the container is empty and within a clearance zone of the package envelope, and wherein the clearance zone is outside a handling zone of the package envelope for automated flat processing by a shipping authority;

retrieving the container and the reply envelope from the package envelope;

collecting the biological specimen in the container after retrieving the container;

inserting the container into the reply envelope after collecting the biological specimen; and shipping the reply envelope to the testing facility after inserting the container.

11. The method of claim 10, wherein the shipping authority is the United States Postal Service.

12. The method of claim 10, further comprising:

inserting the container into a biohazard bag after collecting the biological specimen and before inserting the container into the reply envelope.

* * * * *